(12) United States Patent  (10) Patent No.: US 8,348,970 B2
Janota  (45) Date of Patent: Jan. 8, 2013

(54) MILITARY EMERGENCY TOURNIQUET

(75) Inventor: John Janota, Chesapeake, VA (US)

(73) Assignee: Mark Donald, Norfolk, VA (US)

( * ) Notice: Subject to any disclaimer, the term of this patent is extended or adjusted under 35 U.S.C. 154(b) by 1205 days.

(21) Appl. No.: 11/455,350

(22) Filed: Jun. 19, 2006

(65) Prior Publication Data

US 2007/0005107 A1    Jan. 4, 2007

Related U.S. Application Data

(60) Provisional application No. 60/595,268, filed on Jun. 20, 2005.

(51) Int. Cl.
*A61B 17/00* (2006.01)

(52) U.S. Cl. ..................................................... 606/203

(58) Field of Classification Search .......... 606/201–204; 602/5, 19; 128/876, 878; 2/338; 24/68 R, 24/70 ST, 69 ST, 68 E, 115 H, 302, 170
See application file for complete search history.

(56) References Cited

U.S. PATENT DOCUMENTS

| 1,566,235 A | | 12/1925 | Sheehan | |
|---|---|---|---|---|
| 6,149,618 A | * | 11/2000 | Sato | 602/75 |
| 6,899,720 B1 | | 5/2005 | McMillan | |
| 2005/0273134 A1 | * | 12/2005 | Esposito | 606/203 |

* cited by examiner

*Primary Examiner* — Gary Jackson
*Assistant Examiner* — Eric Blatt
(74) *Attorney, Agent, or Firm* — Schiff Hardin LLP

(57) ABSTRACT

The military emergency tourniquet is a device for rapidly and easily reducing or stopping blood flow to a limb. The tourniquet utilizes a closed loop system and includes a twistable strap, a base including two opposing entry apertures and an exit aperture, a windlass and at least one receiving loop. The twistable strap is slidably positioned through the opposing entry apertures and the exit aperture thereby forming a closed loop. The windlass is positioned outside of the closed loop and is affixed to one end of the strap. The windlass includes an aperture capable of sliding the opposing end of the strap therethrough. The receiving loop receives an end of the windlass and is affixed to the base.

21 Claims, 5 Drawing Sheets

MILITARY EMERGENCY TOURNIQUET

CROSS REFERENCE TO RELATED APPLICATIONS

The present application claims benefit of priority to U.S. patent application Ser. No. 60/595,268 filed on Jun. 20, 2005, entitled, "Military Emergency Tourniquet" and is herein incorporated by reference in its entirety.

TECHNICAL FIELD

The present invention relates generally to the field of medical devices and more specifically to a tourniquet having a closed loop system.

BACKGROUND

Tourniquets are used in medical emergencies to restrict blood flow to a particular limb of a patient. Virtually all known tourniquets include a strap for wrapping around the patient's limb to form a loop. The strap is then tied or buckled to prevent loosening. Some tourniquets also include a rigid tightening rod positioned within the loop for further tightening. Conventional tightening rods are typically secured by methods such as pushing the rod under the tightened loop or in at least one instance by insertion into a pocket assembly slidably positioned along the strap as in U.S. Pat. No. 6,899,710.

Tourniquets are commonly provided to emergency medical personnel and may be found in first aid kits. Since an emergency can happen at any time, tourniquets should be designed for rapid use during the day and night. The present invention addresses these concerns and provides a tourniquet that is quick and easy to use in light or darkness.

SUMMARY

The present invention provides a tourniquet utilizing a closed loop system to rapidly and easily restrict blood flow to a patient's limb without the need of a buckle for securing a strap. In addition the present invention does not require the user to manipulate the position of a securing loop for a tightening rod while tightening the tourniquet. In one aspect of the present invention a tourniquet is provided including a twistable strap, a base including two opposing entry apertures and an exit aperture, a windlass and a receiving loop. The twistable strap is slidably positioned through the opposing entry apertures and the exit aperture of the base. The strap and base together form a closed loop. The windlass is positioned outside of the closed loop and is affixed to one end of the strap. The windlass includes an aperture capable of slidably receiving the opposing end of the strap therethrough. The receiving loop is capable of receiving the windlass and is attached to the base. The tourniquet may also include additional features such as a coating or treatment along a portion of the strap to increase the gripping capability of the strap to a limb. The coating or treatment may therefore reduce potential slipping of the tourniquet along a limb. In some embodiments there are at least two exit apertures, such as one exit aperture for each end of the strap. There may be two receiving loops, one for each end of the windlass. One receiving end may be a fixed length and the second may have an adjustable length.

In another aspect of the present invention a method of restricting blood flow is provided including providing a tourniquet of the present invention, placing the limb of a patient through the closed loop, pulling the end of the strap opposite the windlass until the windlass reaches or nearly reaches the base, twisting the windlass until blood flow is restricted, and inserting at least one end of the windlass in at least one receiving loop.

BRIEF DESCRIPTION OF THE DRAWINGS

The accompanying drawings, which are also incorporated into and as part of the specification, are to assist the reader in comprehending various features of the present invention. The drawings are for illustrative purposes and are not to be construed as limiting the invention.

DETAILED DESCRIPTION

Definitions

The term "entry apertures" as used herein refers to access or entry sites for the strap to enter the base. "Opposing entry apertures" are entry sites positioned at substantially opposite ends of the base where the strap may enter the base.

The term "exit aperture" as used herein refers to one or more apertures allowing the opposing ends of the strap to exit the base and proceed outward or towards the windlass. Upon exit through the exit aperture by both ends of the strap, a closed loop is formed.

The term "closed loop" or "closed loop system" as used herein refers to a strap and base that are slidably engaged such that both opposing ends of the strap are slidably positioned through the entry and exit apertures of the base. A "closed loop" tourniquet requires the patient's limb be inserted through the loop formed by the strap and base. A "closed loop" may be opened by removing the grasping end from the exit aperture and the entry aperture.

The term "slidably positioned" as used herein refers to the ability to slide along a feature or element. The base may slide along the strap and is thus slidably positioned along the strap. The windlass may slide along a portion of the strap and is thus slidably positioned along the strap.

The term "grasping end" refers to the portion of the strap that outside of the closed loop and is pulled to tighten the tourniquet. The grasping end is the end portion of the strap that is opposite the windlass-attached end. The grasping end is slidably inserted through the windlass aperture. The grasping end is not limited to the endpoint of the strap but includes the region of the strap that exits the exit aperture.

The term "attached end" or "windlass-attached end" as used herein refers to the end region of the strap that is attached to the windlass.

Description of Preferred Embodiments

Figure 1:
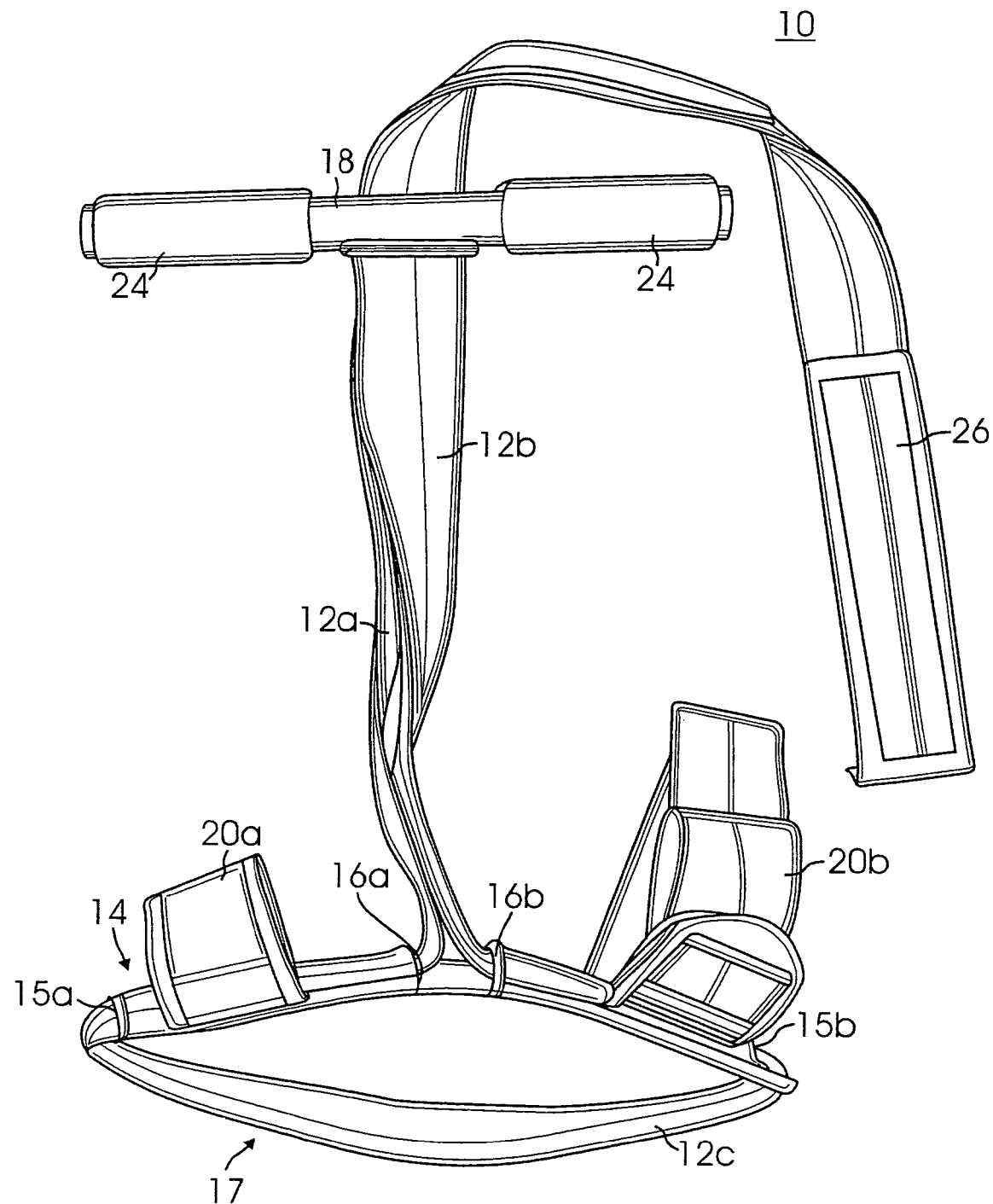
FIG. 1 is a front view of a preferred embodiment of the tourniquet 10 of the present invention showing the strap 12 entering the base 14 through two opposing entry apertures 15a & 15b and exiting the base 14 via two exit apertures 16a & 16b. The windlass 18 is affixed to one strap end 12a and slidably positioned along the opposing strap end 12b, also shown having a reinforced end piece 26. A fixed length receiving loop 20a and an adjustable length receiving loop 20b are affixed to opposing ends of the base 14 and able to receive the windlass 18. The added fastener 24 shown positioned at each end of the windless 18 may assist the retention of the windless 18 within the receiving loops 20.
Figure 2:
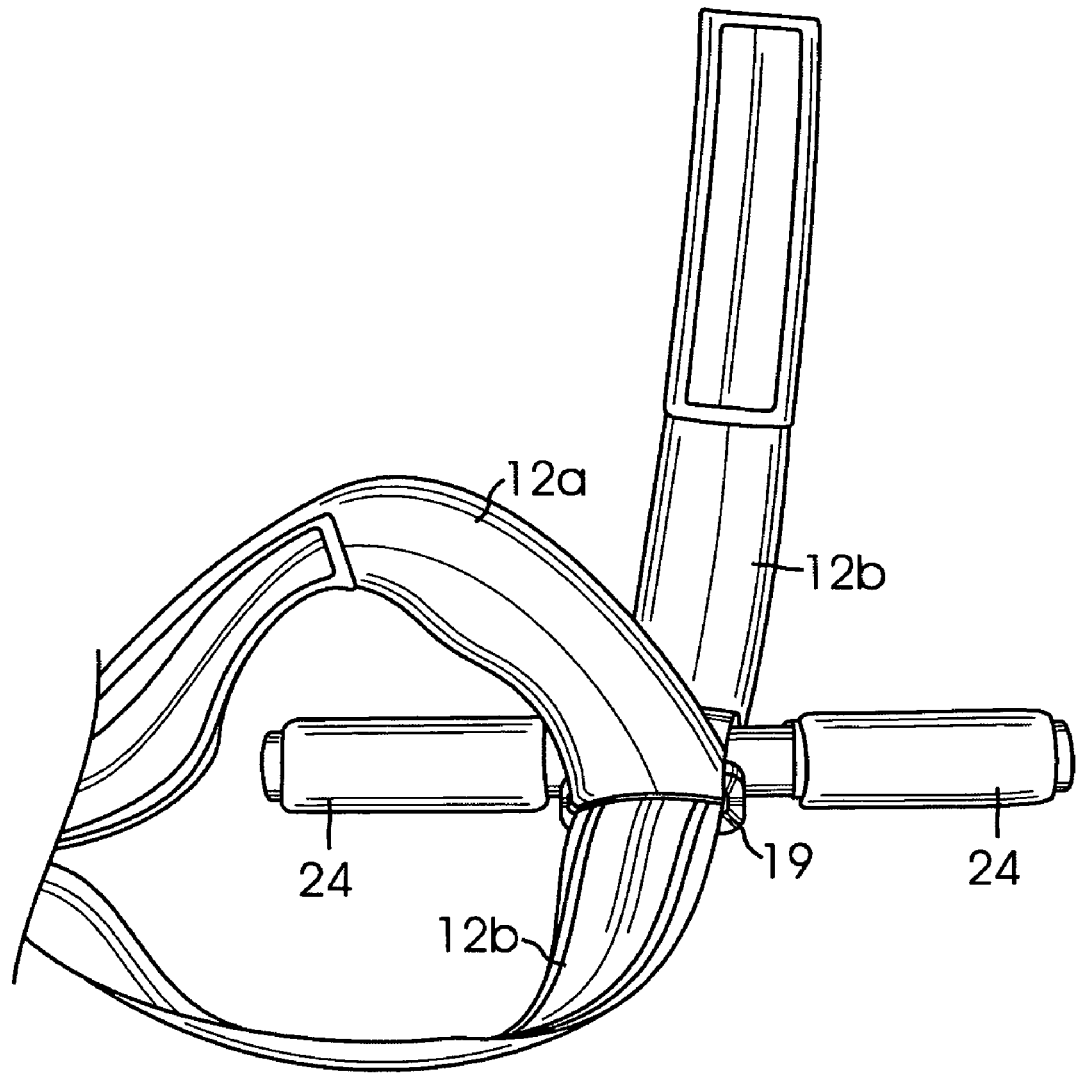
FIG. 2 is a partial perspective view of the device shown in FIG. 1 depicting the attached strap end 12a and the opposing grasping strap end 12b. Also depicted are the windless aperture 19 through which the grasping end 12b is slidably inserted.
Figure 3:
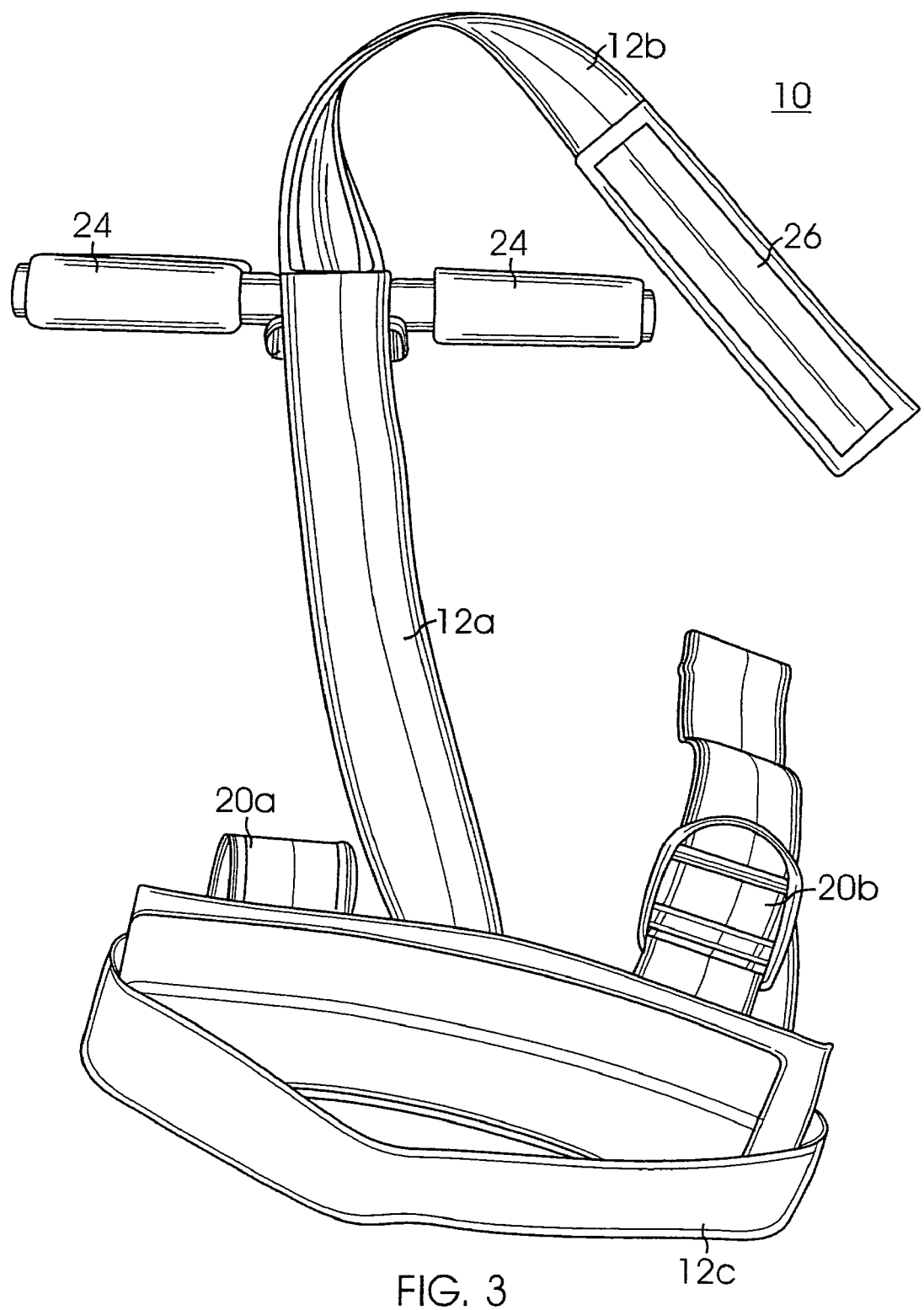
FIG. 3 is a perspective view of the tourniquet 10 shown in FIG. 1, showing the attached first strap end 12a and the opposing strap end 12b.
Figure 4:
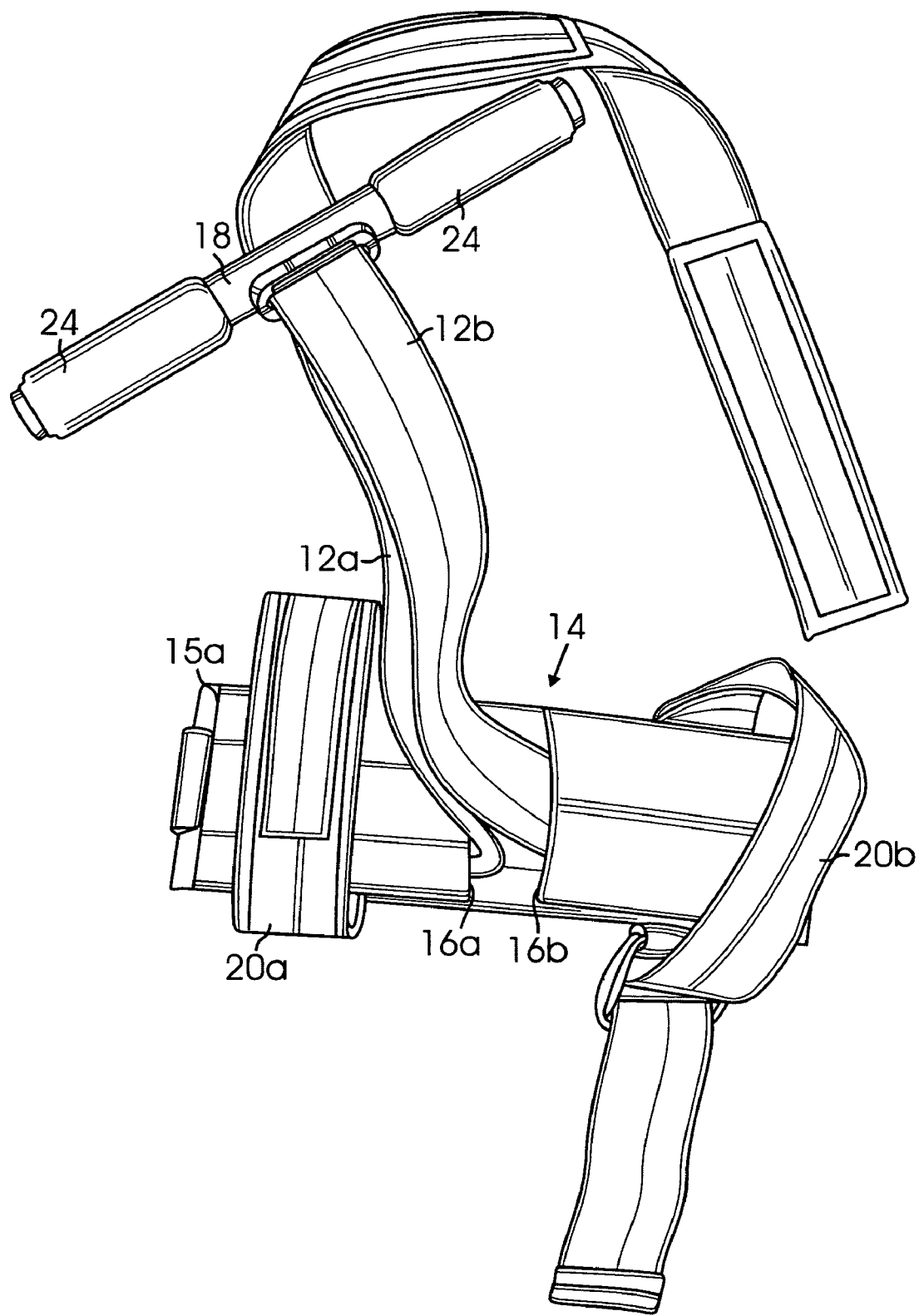
FIG. 4 is perspective view of the device shown in FIG. 1, showing the top of base 14, the two exit apertures 16a & 16b, the fixed length receiving loop 20a and the adjustable length receiving loop 20b.
Figure 5:
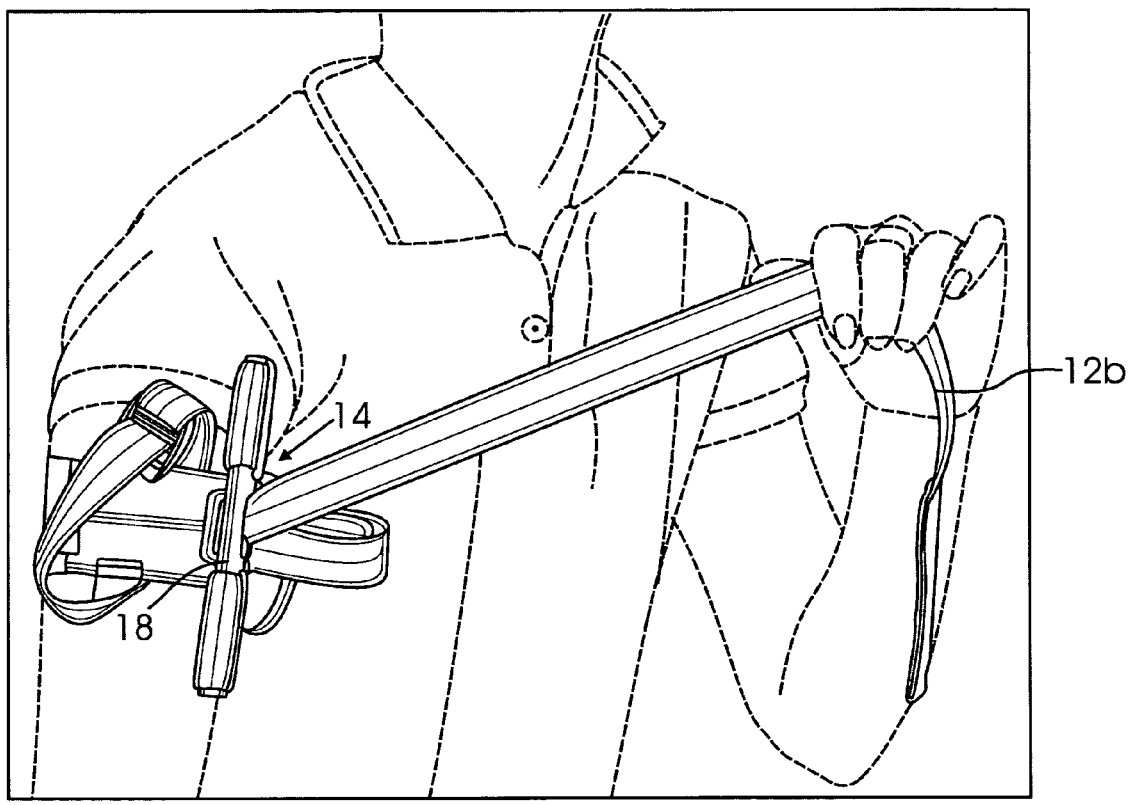
FIG. 5 is a perspective view of the device shown in FIG. 1 being applied to a victim. The grasping end 12b is pulled to slidably position the windlass 18 near the base 14.

Referring to FIGS. 1-5, the present invention provides a military emergency tourniquet 10, the tourniquet 10 of the present invention includes a twistable strap 12 slidably inserted into the base 14 via two opposing entry apertures 15. The strap 12 exits the base 14 via the exit aperture 16. The resulting tourniquet 10 is referred to as having a closed loop system 17, which does not require the use of a buckle to secure the strap 12 or require tying or untying the strap 12 during use. Attached to one of the strap 12a and positioned outside of the closed loop 17 is a windlass 18. The windlass 18 also includes an aperture 19 through which the opposing end of the strap 12b is slidably inserted. Therefore the windlass 18 is attached to one end of the strap 12a and is capable of sliding along the opposing end of the strap 12b. Also included is at least one receiving loop 20 capable of receiving an end of the windlass 18. Since the receiving loop 20 is attached to the base 14, the receiving loop 20 does not require significant manipulated during tightening of the tourniquet 10. The present configuration conveniently places the receiving loop 20 in close proximity of the windlass 18 when the windlass 18 is near or adjacent to the base 14 (when in a tightened position).

The tourniquet 10 of the present invention can be used by a variety of medical personnel, care-givers, security personnel and the like. The tourniquet 10 is suitable for use for the military, police, lifeguards, nurses, doctors, ski patrol and the like. As demonstrated in FIG. 5, the tourniquet 10 of the present invention can even be used by the victim.

The tourniquet 10 can be rapidly placed on the patient and removed. Use of the tourniquet 10 may include inserting a limb through the closed loop 17, grasping and pulling the strap end 12b opposite the windlass 18 until the windlass 18 is slidably positioned near the base 14, twisting the windlass 18 causing the strap 12 to twist upon itself, which shortens the strap 12, then inserting at least one end of the windlass 12 into a receiving loop 20. The tourniquet 10 may be removed by releasing the windlass 18 from the receiving loop 20, substantially unwinding the windlass 18 and pulling the windlass 18 away from the base 14 thereby adding slack to the closed loop system 17 and removing the limb from the closed loop 17.

The strap 12 allows the regulation of a patient's blood flow to a limb. Regulation may include restricting or stopping blood flow to the limb. In one preferred embodiment the strap 12 is maintained in a closed loop system 17. In this configuration, the patient's limb is placed through the closed loop 17. The strap 12 is typically first tightened by pulling on one end of the strap 12b, also referred to as the grasping end 12b. Since the windlass 18 is slidably positioned along the grasping end 12b, pulling the grasping end 12b results in the windlass 18 being slidably moved towards the base 14. The strap 12 can be further tightened by twisting the windlass 18, which forces the strap 12 to twist upon itself thereby further decreasing the diameter of the closed loop 17. In another embodiment, the tourniquet 10 is opened then closed around a limb.

The strap 12 is preferably constructed from a twistable or foldable material such as nylon webbing or nylon strapping such as those used in the camping, luggage and pet industries.

The strap 12 should be sufficiently long to encircle a desired limb while also providing enough remaining material to have at one end 12a an attached windlass 18 and at the opposing end 12b enough material to grasp and pull for tightening of the tourniquet 10. The strap 12 may be cut to the desired size using conventional cutting techniques known in the manufacturing arts. As general guidance, the preferred strap 12 is about 24 inches to about 36 inches in length. However, an individual with a larger limb, such as a large adult's leg, may require a longer strap 12 (e.g. a length preferably from about 36 inches to about 44 inches) and an individual with a smaller limb, such as a child's arm, may not require as long of a strap 12 (e.g. 8 inches to about 24 inches). The width of the strap 12 may vary depending on the strength of the material used. In the preferred embodiments, a nylon strap 12 has a width of about one inch. However, the strap 12 may be less than one inch wide, three to five inches wide or more if desired. A strap 12 may include a coating or treatment for enhanced gripping of a limb. As a non-limiting example, a rubber-based material such as rubber or TUFF-TEC to provide added grip against a limb. Materials may be adhered to or coated on an inner surface the strap 12 using conventional techniques known in the fabric industries such as weaving, sewing, gluing, melting then cooling and the like.

At one end of the strap 12a, is attached the windlass 18. In one embodiment, the end of the strap 12a is inserted through the windlass aperture 19, returned and sewn upon itself such that the windlass 18 is attached via a sewn loop. In other non-limiting embodiments the strap 12a may be tied, buckled, snapped or clipped to the windlass 18. Either end or both ends of the strap 12a/12b may be reinforced, such as being doubled back and sewn or by attaching additional fabric or materials to the strap 12.

The end of the strap 12b opposite the windlass 18, also referred to as the grasping end 12b, is used to tighten the tourniquet 10. The grasping end 12b may have a reinforced end piece 26 or may be provided with an end loop for ease of grasping. The end loop may be configured for a single finger, two or more fingers, a hand or the like. When the grasping end 12b is pulled, tension causes the windlass-attached end of the strap 12a to slide towards the base 14. The windlass 18 prevents the attached end of the strap 12a from sliding out from the base 14 and opening the closed loop 17. The remaining strap portion 12c is within the closed loop 17.

The base 14 in combination with the strap 12 forms the closed loop system 17. The base 14 is preferably an elongated segment of nylon webbing or reinforced nylon webbing. The base 14 is typically more rigid than the strap 12 and may be constructed from a thicker material or may be a reinforced material. In preferred embodiments, the base 14 has a width of about six inches long by about two inches wide however these measurements are not limiting to the present invention. For example, the base 14 may be 2"×2", 4"×4", 4"×2", 8"×4" and the like. The base 14 may be cut to the desired size using conventional cutting techniques known in the manufacturing arts. The base 14 includes two opposing entry apertures 15a & 15b through which the opposing ends of the strap 12a & 12b are slidably positioned and at least one exit aperture 16 for the exit of the opposing ends of the strap 12a & 12b. In one embodiment, the base 14 is constructed by providing a bottom segment of nylon webbing approximately 6"×2" and gluing or stitching to the top and at opposing ends, two separate nylon webbing pieces about 2"×2¾". The stitching or gluing performed along two of the four perimeter regions of the two top segments forming two entry apertures 15a & 15b and two exit apertures 16a & 16b. Alternatively, a single top segment may be slit at about the middle to form a single exit aperture 16 and two of the four perimeter regions sewn or glued to the bottom segment forming two entry apertures 15a & 15b. In the preferred embodiment the strap 12 exits the exit aperture 16 generally perpendicular to the base 14. The slidability of the base 14 may be adjusted by adjusting the space between the top segment(s) and the bottom segment and/or the size of the entry apertures 15 and exit aperture(s) 16.

The windlass 18 not only allows the strap 12 to be further tightened and therefore helps restrict blood flow but can also function as a handle to release the tension from the strap 12. The windlass 18 is attached to one end of the strap 12a, also referred to as the windlass-attached end 12a or attached end 12a, and includes an aperture 19 for slidably mounting the windlass 18 to the opposing end 12b, also referred to as the grasping end of the strap 12b. Pulling the grasping end of the strap 12b transfers the windlass 18 towards the base 14. The windlass 18 can then be rotated or wound, which causes the strap 12 to decrease the diameter of the closed loop 17. Once blood flow is reduced or halted. At least one end of the windlass 18 may be inserted into a receiving loop 20, which is attached to the base 14. The receiving loop 20 prevents a wound windlass 18 from unwinding. In the preferred embodiment, both ends of the windlass 18 and a portion of a single receiving loop 20 include complementary fasteners 24, such as interlocking hook and loop structures functioning similar to VELCRO. In this embodiment, the complementary fasteners 24 assist in securing the windlass 18 to the receiving loop 20. Both ends of the windlass 18 may be secured by receiving loops 20.

After use, the strap 12 may be loosened using the windlass 18. The windlass 18 may be substantially unwound then grasped and pulled away from base 14. Since one end of the strap 12a is attached to the windlass 18, pulling a substantially unwound windlass 18 also pulls the strap 12, which causes slack in the closed loop 17. Therefore the strap 12c loosens from the limb. The strap 12c can be further loosened by pulling on a portion of the strap 12c that makes up the closed loop 17 so long as the windlass is substantially unwound. The limb can then be removed.

The windlass 18 should be sufficiently strong to withstand the twisting of the strap 12. Non-limiting examples of suitable materials include plastic, metal, metal alloy, carbon fiber, wood and the like. Materials that do not rust or are treated with compound to prevent rusting may be preferred if stored or used in a moist environment. In a preferred embodiment aluminum is used. In the preferred embodiment the windlass 18 has a rod configuration having a length of about six inches and a diameter of about one half inch. The windlass 18 may be cut to the desired length using conventional cutting techniques known in the manufacturing arts. In the preferred embodiment, the windlass 18 includes an aperture 19 positioned generally at the center of the rod. The aperture 19 should be sufficiently large that the strap 12b can be slidably inserted therethrough yet be able to force the strap 12 to twist when the windlass 18 is wound. In the preferred embodiment the strap 12 has a width of about one inch and the aperture 19 is an elongated aperture having a width of about one and one-eighth inch. The aperture 19 may be formed using conventional drilling or slot forming techniques known in the manufacturing arts.

The receiving loop 20 prevents a wound windlass 18 from unwinding. The receiving loop 20 is attached to the base 14. Since the receiving loop 20 is attached to the base 14 it is conveniently positioned for a wound windlass 18. In other words, the present invention does not require pre-positioning or adjusting the position of the receiving loop 20 along the strap 12 during the tightening procedure, which facilitates the rapid and ease of use of the tourniquet 10. One or more receiving loops 20 may be constructed. The receiving loop 20 may be constructed from any suitable material. The material should be bendable or foldable. Suitable examples of materials include but are not limited to nylon webbing. The receiving loop 20 may be attached to the base 14 using any conventional attachment technique such as sewing, gluing, snapping and the like. The receiving loop 20 may be reinforced with additional material.

In the preferred embodiment, a first receiving loop 20 having a diameter of about two to three inches is sewn to the base 14. To an inner portion of the first receiving loop 20a is attached a portion of a hook and loop fastening means 24 for releasably fastening the windlass 18. A second loop 20b is attached (e.g. sewn) to the base 14 opposite the end of the first loop 20a. The second loop 20b includes an adjustable diameter from about three or four inches to essentially no diameter, which essentially results in the second loop 20b laying substantially flat along the top surface of the base 14. The adjustment of a receiving loop 20, such as the provided second receiving loop 20b, may use any conventional adjusting techniques such as hook and loop, slides, triglide buckles, adjustable clips, slide release buckles and the like. In the preferred embodiment a Fastex LADDERLOC adjusting structure is used for adjusting the second receiving loop 20b.

The present invention also includes a method of using a tourniquet 10 including providing a tourniquet 10 of the present invention, inserting a victim's limb through the closed loop 17, pulling the end of the strap 12b opposite the windlass 18 until the windlass 18 reaches or nearly reaches the base 14, twisting the windlass 18, and inserting at least one end of the windlass 18 into a receiving loop 20.

After the desired medical treatment, the windlass 18 is removed from the receiving loop 20. The windlass 18 is substantially unwound then pulled to provide slack in the closed loop 17. The closed loop 17 is widened to permit exit of the limb.

What is claimed is:

1. A tourniquet, comprising:
a) a twistable strap having first and second ends;
b) a base comprising two entry apertures at opposite ends of said base and an exit aperture, wherein said twistable strap is slidably positioned through said entry apertures and said exit aperture thereby forming a closed loop;
c) a windlass positioned outside said closed loop, said windlass affixed to said first end of said twistable strap, said windlass defining an aperture through which extends said second end of said twistable strap so as to permit sliding of the second end of said twistable strap through said aperture so that pulling on said second end of said twistable strap decreases a diameter of said closed loop, said first end of said strap being affixed to said windlass so as to extend through said aperture, said aperture having a length and width conforming generally to a shape of said strap so as to prevent rotation of said second end of said strap in said aperture during twisting of said windlass, said windlass being rotatable to twist said first and second ends of said twistable strap on one another to form a twisted portion and thereby constrict said closed loop, said twisted portion of said twistable strap extending from said exit aperture of said base;
d) a receiving loop for receiving an end of said windlass when said twistable strap is in a twisted condition, said receiving loop affixed to said base.

2. The tourniquet according to claim 1, wherein said twistable strap is constructed from nylon webbing.

3. The tourniquet according to claim 1, wherein an interior portion of said closed loop comprises a gripping structure, said gripping structure at said second end of said strap bearing against said first end of said strap at said aperture.

4. The tourniquet according to claim 1, wherein said gripping structure is a rubber based material.

5. The tourniquet according to claim 1, wherein said base is formed as a sandwich configuration comprising an upper portion of nylon webbing sewn along two of four perimeters to a lower portion of nylon webbing and an opening formed in said upper portion to define said exit aperture.

6. The tourniquet according to claim 5, wherein said exit aperture comprises two exit apertures, wherein each of said two exit apertures provides an exit for a corresponding one of said two entry apertures.

7. The tourniquet according to claim 6, wherein said upper portion comprises two upper portions of nylon webbing, said two upper portions being sewn to said lower portion to form two passageways through which respective ones of said first and second ends of said strap are slidably disposed.

8. The tourniquet according to claim 1, wherein said strap exits said exit aperture approximately perpendicular to said base.

9. The tourniquet according to claim 1, wherein said windlass is a rod.

10. The tourniquet according to claim 1, wherein said windlass is a rod of a material selected from the group consisting of plastic, metal, carbon fiber and metal alloy.

11. The tourniquet according to claim 1, further comprising complementary portions of a hook and loop fastener attached on one hand to said windlass and on the other hand to said receiving loop such that said windlass can be fastened to said receiving loop by said hook and loop fastener.

12. The tourniquet according to claim 1, wherein said aperture in said windlass is an elongated aperture.

13. The tourniquet according to claim 1, wherein said windlass is attached to said strap by feeding said strap through said aperture of said windlass and attaching said strap to itself by connecting a fed portion of said strap to an unfed portion of said strap to form a loop through said aperture.

14. The tourniquet according to claim 1, wherein said base is constructed of nylon webbing.

15. The tourniquet according to claim 1, wherein said base includes first and second sleeves through which are slidably disposed first and second ends of said twistable strap.

16. A tourniquet for application about a limb of a patient, comprising:
a strap having first and second ends;
a base of a flexible material having opposite ends, said base having first and second sleeves in alignment with one another, said first and second sleeves having respective entry openings at said opposite ends of said base and having exit openings adjacent one another and spaced from said opposite ends, said strap passing through said first and second sleeves of said base so that said first and second ends extend from respective ones of said exit openings and so that a portion of said strap extending from said entry openings forms a loop with said base ;
a windlass connected to a first end of said strap, said windlass defining an aperture through which passes said second end of said strap in sliding relation so that pulling on said second end of said strap will decrease a diameter of said loop, said windlass being rotatable to twist said strap to thereby reduce a diameter of said loop;
said first end of said strap being connected to said aperture of said windlass by being looped through said aperture so as to be disposed in side-by-side relation with a portion of said second end of said strap that passes through said aperture of said windlass, said first end of said strap being in contact with said second end of said strap at said aperture, said aperture having a length and width conforming generally to a cross-sectional shape of said strap so as to prevent said second end of said strap from twisting in said aperture during twisting of said windlass and thereby maintain said first end of said strap and said second end of said strap in side-by-side relation as said windlass is twisted; and
a receiving loop on said base positioned to receive said windlass when said windlass has been rotated to twist said strap so that said receiving loop holds said windlass to resist untwisting of said strap.

17. A tourniquet as claimed in claim 16, wherein said first and second ends of said strap pass through said aperture of said windlass and are in side-by-side contact at said aperture.

18. A tourniquet as claimed in claim 17, wherein said first end of said strap is connected to said windlass by looping said first end through said aperture of said windlass and securing said first end to said strap to form a second loop encircling a portion of said windlass at one side of said aperture.

19. A tourniquet as claimed in claim 16, wherein said receiving loop is a first receiving loop, and further comprising:
a second receiving loop on said base, said first and second receiving loops being disposed on opposite sides of said exit apertures to receive opposite ends of said windlass.

20. A tourniquet as claimed in claim 19, wherein said second receiving loop includes a securing buckle and strap.

21. A tourniquet for application about a limb of a patient, comprising:
a strap having first and second ends, said first end of said strap including a first loop;
a windlass in a shape of an elongated rod and defining an elongated aperture in said rod, said first loop of said first end of said strap encircling a portion of the windlass at one side of said aperture so as to connect said first end of said strap to said windlass, said second end of said strap extending in sliding relation through said aperture in said windlass so as to be disposed in side-by-side relation with said first end of said strap and to thereby form a second loop of said strap, said aperture being of a shape so that said first end of said strap and said second end of said strap are in contact with one another in said aperture, said sliding relation of said second end of said strap through said aperture causing said second loop to decrease in diameter when said second end of said strap is pulled, said windlass being rotatable to twist said strap at the portions thereof disposed in side-by-side relation to form a twisted portion to thereby reduce a diameter of said second loop;
a base affixed in sliding relation to said strap at the twisted portion to prevent capture of skin or clothing during twisting of windlass when said second loop is disposed about a limb of the patient; and
a windlass retaining member on said base, said windlass retaining member being selectively engagable to said windlass to hold said windlass so as to resist untwisting of the twisted portion of said strap.

* * * * *